United States Patent [19]

Maeda et al.

[11] Patent Number: 4,594,879
[45] Date of Patent: Jun. 17, 1986

[54] THERMAL CONDUCTIVITY DETECTOR

[75] Inventors: Masato Maeda; Shuzo Kawamura, both of Tokyo, Japan

[73] Assignee: Yokogawa Hokushin Electric Corporation, Tokyo, Japan

[21] Appl. No.: 544,064

[22] Filed: Oct. 21, 1983

[30] Foreign Application Priority Data

Oct. 28, 1982 [JP] Japan .............................. 57-189551
Oct. 29, 1982 [JP] Japan .......................... 57-164150[U]

[51] Int. Cl.⁴ ........................................... G01N 25/18
[52] U.S. Cl. ..................................... 73/27 R; 73/204
[58] Field of Search ................. 73/27 R, 204; 374/43, 374/179

[56] References Cited

U.S. PATENT DOCUMENTS

| | | | |
|---|---|---|---|
| 2,585,959 | 2/1952 | Minter | 73/27 R |
| 3,474,660 | 10/1969 | Dooley | 73/27 R |
| 3,603,134 | 9/1971 | Norem | 73/27 R |
| 4,185,490 | 1/1980 | Clouser et al. | 73/27 R |

FOREIGN PATENT DOCUMENTS

| | | | |
|---|---|---|---|
| 425518 | 7/1924 | Fed. Rep. of Germany | 73/27 R |
| 326499 | 3/1972 | U.S.S.R. | 73/27 R |

Primary Examiner—David L. Lacey
Attorney, Agent, or Firm—Moonray Kojima

[57] ABSTRACT

A thermal conductivity detector of the type that uses an electrical bridge of four heaters with the fluid to be measured being exposed to a pair of heaters and the reference fluid being exposed to the other pair of heaters, wherein the invention improves upon this type of detector by having the fluid to be measured applied to a pair of parallel passageways in a block structure wherein a pair of heaters are contained and concurrently into bypass passageways which bypass the pair of heaters and then outputted through a common outlet; and wherein concurrently the reference fluid is applied to a pair of parallel passageways in another block structure wherein another pair of heaters are contained and concurrently to bypass passageways which bypass the second pair of heaters and then outputted through a common outlet and wherein the bypass passageways of one of the block structures are different in internal diameter from the bypass passageways in the other block structure. This invention enables rapid detection without being adversely affected by changes in quantities of fluid being measured.

2 Claims, 16 Drawing Figures

THERMAL CONDUCTIVITY DETECTOR

BACKGROUND OF THE INVENTION

1. Field of the Invention

This invention relates to a thermal conductivity detector designed to detect an unbalanced voltage generated in a bridge comprising first through fourth heaters by detecting the thermal conductivity of fluid being examined and supplied to the first and second heaters, the thermal conductivity detector being fit in, for instance, a gas chromatograph and used to measure the concentration of constituents contained in the fluid being examined.

2. Description of Prior Art

FIG. 1 is an explanatory drawing illustrating an example of use of a conventional thermal conductivity detector. In FIG. 1, there are shown first, second, third, and fourth cells 1,2,3,4, respectively, containing first-,second, third and fourth heaters 1a,2a,3a, and 4a, respectively. Fluid being examined is led from an inlet 5a (see arrow) of the first cell 1, made to flow through first cell 1 and second cell 2, and led out of an outlet 5b (see arrow) of second cell 2. A reference fluid is led from an inlet 6a (see arrow) of third cell 3, made to flow through third cell 3 and fourth cell 4, and led out of an outlet 6b (see arrow) of fourth cell 4. In addition, first, second, third and fourth heaters 1a,2a,3a and 4a, are connected to form an electrical bridge 7 and a predetermined current is supplied from a constant current supply 8 to bridge 7.

When an unbalance voltage is generated in bridge 7, a detection circuit 9 will detect such unbalance voltage, and in that way, variation in thermal conductivity of the fluids being examined can be measured. Moreover, first, second, third, and fourth cells 1,2,3 and 4, may be of any of the following types: direct flow type cells, shunt direct type cells, diffusion type cells, or semi-diffusion type cells.

Although the use of the direct flow type cell quickens detection response, one disadvantage to such direct flow type cell is that such cell is too sensitive and responds to fluctuations in the quantity of the flowing fluid being examined and the reference fluid. Thus, noise is allowed to be readily generated.

On the other hand, although diffusion type cells do not generate much noise in a detected signal despite fluctuations in the flowing quantities as described above, use of diffusion type cells is disadvantageous because detection response is slow and a sudden change in the thermal conductivity of the fluid being examined cannot be readily followed up.

For these reasons, either type of cells must be selected depending on the intended use. At the same time, generally unsuccessful attempts have been heretofore made, to introduce a thermal conductivity detector which is quick in detection response and which is capable of suppressing such noise. Thus, there is a need in the art for an improved detector having quick response without any substantial noise problem.

SUMMARY OF THE INVENTION

Accordingly, an object of the invention is to overcome the aforementioned and other deficiencies and disadvantages of the prior art.

Another object is to provide a thermal conductivity detector which is not substantially affected by fluctuating flow quantities of fluid being examined, and which is capable of rapid detecting of the thermal conductivity of the fluid.

The foregoing and other objects are attained by the invention which encompasses a thermal conductivity detector comprising first and second flow passages wherein a fluid being examined and a reference fluid are respectively made to flow with the first and second flow passages being constructed of first and second cells having particular internal structure different from each other and wherein in a first condition the first and second cells are respectively used as first and second flow passages, and in a second condition, the first and second cells are respectively used as second and first flow passages.

DESCRIPTION OF PREFERRED EMBODIMENTS

Figure 2:
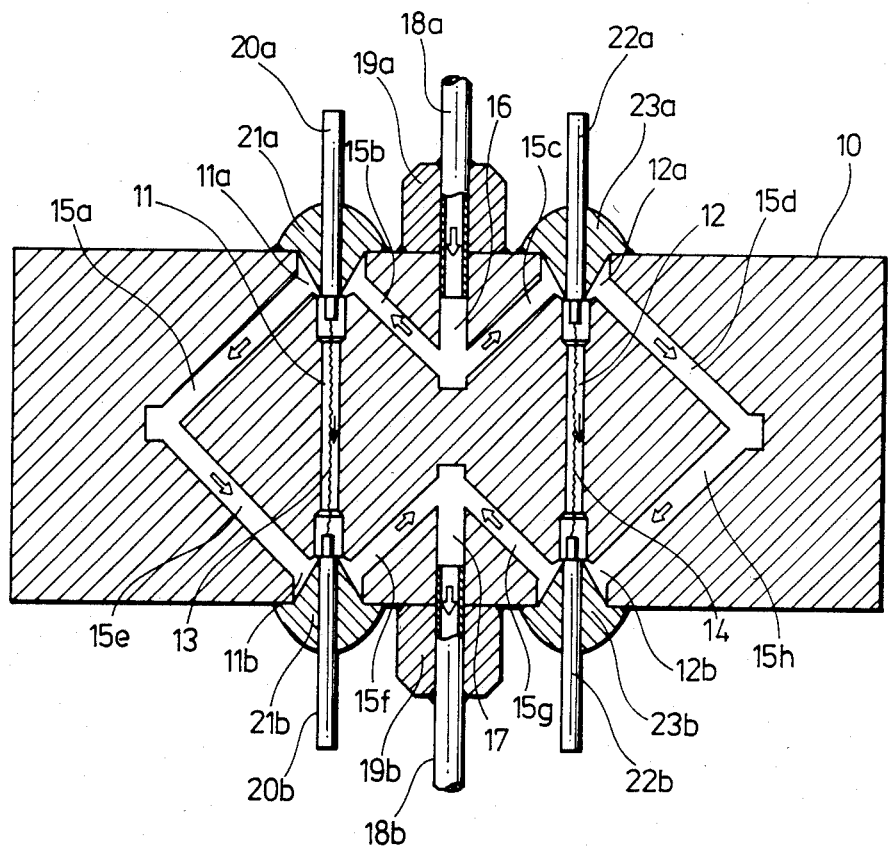
FIGS. 2 and 3 are cross sectional views depicting principal portions of an illustrative embodiment of the invention.
Figure 3:
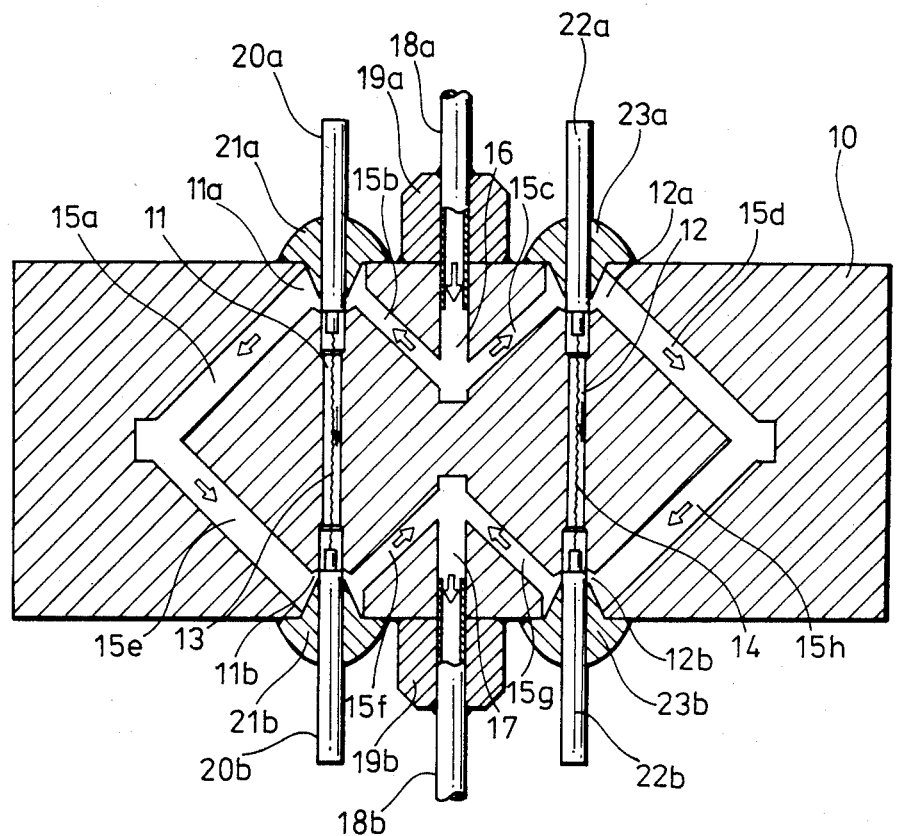
Figure 4:
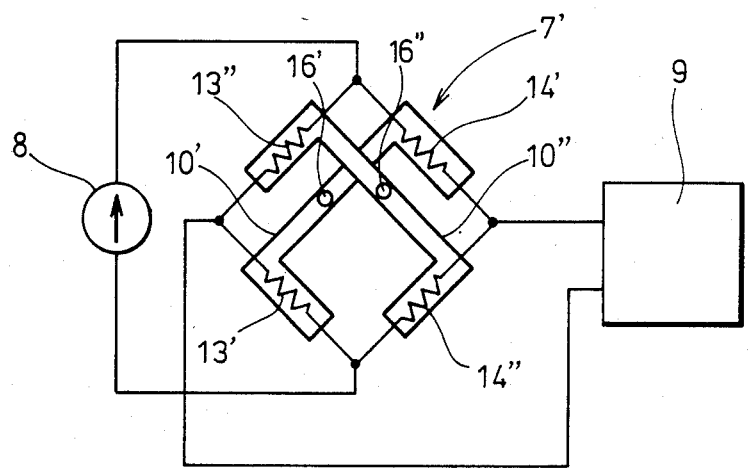
FIG. 4 is an explanatory drawing depicting use of an illustrative embodiment of the invention.

FIGS. 2 and 3 depict cross sectional views of principal portions of an illustrative embodiment of the invention. There are two cells, with the cell of FIG. 3 having larger internal passageway cross sections than that of FIG. 2. In operation the heating coils of the two cells are suitably connected together to form an electrical bridge, as shown in FIG. 4. Also, by suitable and selective connections, in one condition, the reference fluid can be supplied to flow through, for example, the cell of FIG. 3 with the fluid to be measured to be supplied to flow through, for example, the cell of FIG. 2. Then, in another condition, by suitable and selective connections, the reference fluid can be supplied to flow through the cell of FIG. 2, with the fluid to be measured supplied to flow through the cell of FIG. 3. Thus, the instant invention is versatile and flexible in use.

Turning to FIGS. 2 and 3, first and second through holes 11 and 12, are made in a block 10, made, for example, of aluminum, in parallel with each other, and heaters 13 and 14, formed of filaments, are inserted in respective through holes 11 and 12.

First, second, third and fourth internal flow passages 15a, 15b, 15c and 15d, are made and respectively extended from the inflow holes 11a,12a of through holes 11 and 12, in both directions forming an angle of about 45°, with the through holes 11,12, with fifth, sixth, seventh and eighth internal flow passages 15e, 15f, 15g and 15h being made and respectively extended from discharge holes 11b and 12b, in both directions forming an angle of about 45° with through holes 11 and 12. The internal flow passages 15e–15h and 15a–15d, are respectively coupled to form flow passages in the shape substantially of a letter W, and at the same time, the first and fourth passages 15a and 15d are coupled to the fifth and eighth internal passages 15e and 15h, to form bypass flow passages when the first and second through holes are used as the main flow passages. Moreover, an inlet 16 for leading a desired fluid to the connection of the second and third internal passages 15b and 15c, and an outlet 17 for discharging the fluid from the connection of the sixth and seventh internal passages 15f and 15g, are inserted roughly in parallel with the first and second through holes 11 and 12. An inlet pipe 18a for leading fluid into inlet 16 and an outlet pipe 18b for discharging fluid from outlet 17, are respectively inserted in inlet 16 and outlet 17. The pipes 18a and 18b may be allowed to penetrate into reinforcing members 19a, 19b (which may for example be similar to beads on an abacus) so as to prevent these pipes 18a and 18b from being bent, and fixed to block 10. The first and second heaters 13,14 are respectively connected to leads 20a,20b and 22a and 22b and in addition may be provided with hermetic seals (such as by seals 21a,21b, and 23a,23b) so that they are sealed in preset positions within first and second through holes 11 and 12 and in the block 10. FIGS. 2 and 3 illustrate that first and fifth internal flow passages 15a and 15e and fourth and eighty internal flow passages 15d and 15h forming bypass passages for first and second through holes 11 and 12, are identical with each other in shape and construction, except that the internal diameters of those shown in FIG. 3 are larger.

In the illustrative embodiment of the detector thus for described (as shown in FIGS. 2 and 3) when a predetermined fluid (which may be either fluid being examined or reference fluid) is supplied to inlet 16, the fluid is divided into two parts after it has passed through inlet 16 (see arrows) and caused to flow in second and third internal passages 15b and 15c. In addition, the fluid is further divided into two parts after it has passed through second internal passage 15b and made to flow in the first through hole 11 and the first and fifth internal passages 15a and 15e and again flow together in the sixth internal flow passage 15f (see arrow). In the same way, the fluid flowing through the third internal flow passage 15c is further divided into two and made to flow through the second through hole 12 and the fourth and eighth internal flow passages 15d and 15h, before flowing together in the seventh internal passage 15g. The fluid flowing through the sixth and seventh internal passages 15f and 15g further again flow together and is discharged from block 10 through outlet 17.

Figure 1:
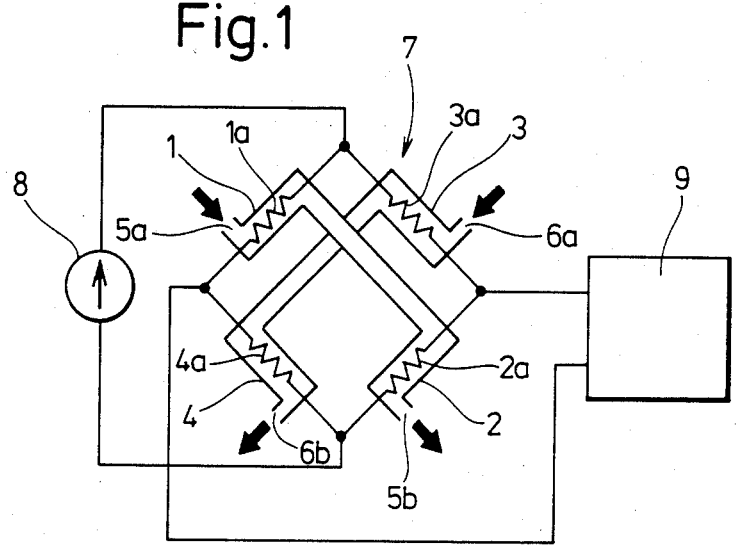
FIG. 1 is an explanatory drawing depicting use of a conventional thermal conductivity detector.

FIG. 4 is an explanatory drawing illustrating an example of use of the illustrative embodiment of the present invention, namely, the use together of the cells of FIG. 2 and FIG. 3. In FIG. 4, like characters designate like parts in FIGS. 1, 2 and 3; and the description thereof is omitted for the sake of clarity of description and simplicity. Numerals 10′,13′,14′ and 16′, and 10″,13″,14″ and 16″, represent similar elements corresponding to block 10, heaters 13 and 14, and inlet 16 in FIG. 2 and block 10, heaters 13 and 14 and inlet 16 in FIG. 3. First and second pipes for leading the fluid being examined and the reference fluid, may, respectively, be connected to inlets 16′ and 16″ (this condition or alternative connection may be called the first condition) or in the alternative, the inlets 16″ and 16′ (this condition or alternative connection may be called the second condition) because the connection of the pipes is changed over or because of the switchover of the flow passages by use of a flow passage selector valve positioned and arranged with respect to inlets 16′ and 16″ to provide the switch flow. To put this another way, in a first condition, for example, the fluid being examined will flow through one cell and the reference fluid will flow through the other cell; and in a second condition, the fluid being examined will flow through the other cell, and the reference fluid will flow through the one cell. A number of test runs for the same sample fluid being tested can be run using first the one cell and then the other cell, and then the runs can be, advantageously, averaged.

A predetermined current is supplied by constant current supply 8 to bridge 7′, comprising heaters 13′,13″,14′, and 14″. An unblanced voltage generated in bridge 7′ is detected in detection circuit 9. In this manner, fluctuations in the thermal conductivity of the fluid being tested can be measured. Also, the constant current supply 8 may be replaced by other types of sources, such as, for example, a constant voltage supply capable of supplying the predetermined current to bridge 7′.

Figure 5A:
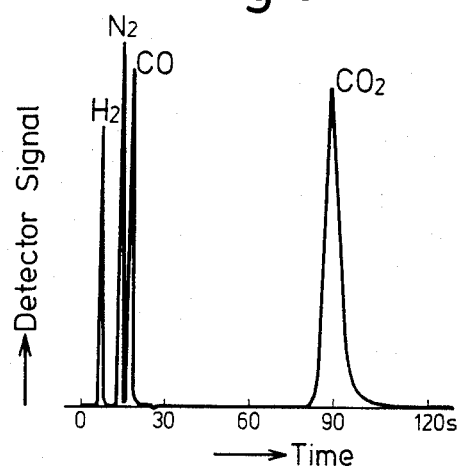
FIGS. 5A, 5B and 5C are chromatograms showing comparisons between response characteristics of a conventional thermal conductivity detector and the invention.

FIGS. 5A through 7 depict test results obtained by comparing the characteristics of a conventional thermal conductivity detector with those of an illustrative embodiment of the invention. FIGS. 5A and 6A indicate the characteristics obtained by using the present invention. FIGS. 5B and 6B depict characteristics obtained by using a conventional direct flow type cell. FIGS. 5C and 6C illustrate characteristics obtained by using a conventional diffusion type cell.

Figure 5B:
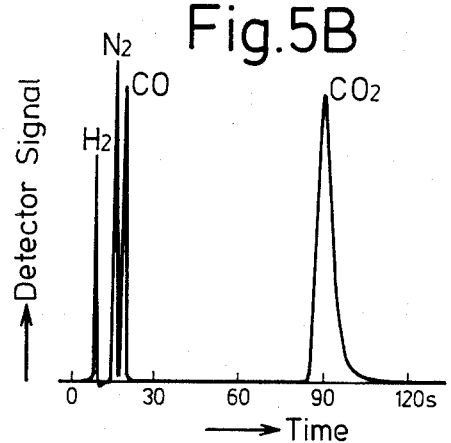
Figure 5C:
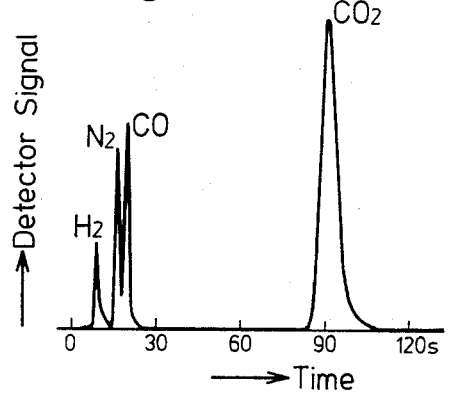

FIGS. 5A, 5B and 5C depict chromatograms obtained by installing a thermal conductivity detector in a process gas chromatograph, to compare response characteristics of the thermal conductivity detector and measuring components ($H_2$, $N_2$, and CO) giving a sharp peak with a short eluting time and a component ($CO_2$) giving a wide peak with a long eluting time.

In preparing the chromatograms, the tests were conducted by maintaining the following operating conditions of the process gas chromatograph:
temperature of thermosatic chamber, 65° C.
carried gas, He
carrier gas pressure, 3.0 Kg.f/cm$^2$
carrier gas flux on measured fluid side, 57 ml/min.
carrier gas flux on reference fluid side (flux of reference fluid), 15 ml/min.
quantity of fluid being examined and collected for each measurement, 50 ml.
composition of fluid being examined, $H_2$=7.21%; $N_2$=42.39% CO=24.7% and $CO_2$=25.7%
Recorder range set common to all detectors.

Figure 6A:
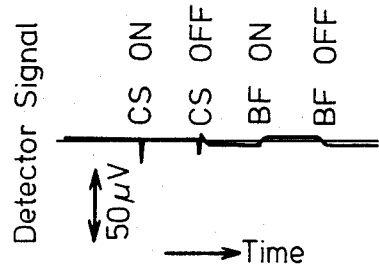
FIGS. 6A, 6B, and 6C are chromatograms showing comparisons between a conventional thermal conductivity detector and the invention, in terms of noise generated in actual use.
Figure 6B:
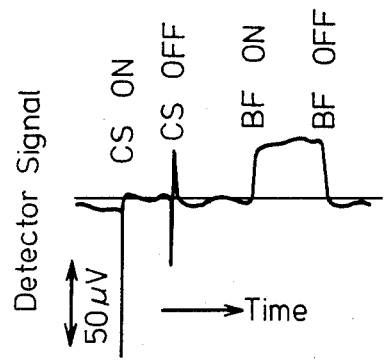
Figure 6C:
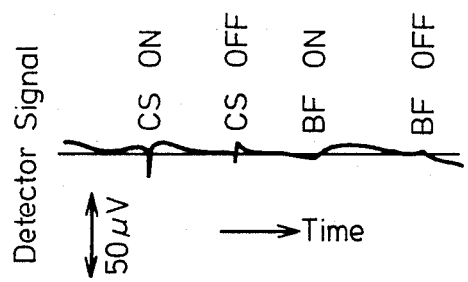

FIGS. 6A, 6B and 6C, are chromatograms (base lines) indicating records of noises generated according to use of selector valves for switching the flow passages of the fluid being supplied to the thermal conductivity detector, in order to compare the noises the thermal conductivity detector is most likely to produce in view of utility.

In preparing the chromatograms, the tests were conducted by maintaining the following operating conditions of the process gas chromatograph equipped with a column switch valve (hereinafter called "CS") used to switch from one column to another and a back flush valve (hereinafter called "BF") used to back flush a respective column:

temperature of thermostatic chamber, 65° C.
carrier gas, N$_2$
carrier gas pressure, 4 kg.f/m$^2$
carrier gas flux on measured fluid side, 40 ml/min
carrier gas flux on reference fluid side (flux of reference fluid), 31 ml/min.

The noises caused by the switching of the valves in FIGS. 6A,6B, and 6C, can be indicated in the form of magnitude of influence of flow fluctuations (stability).

Figure 7:
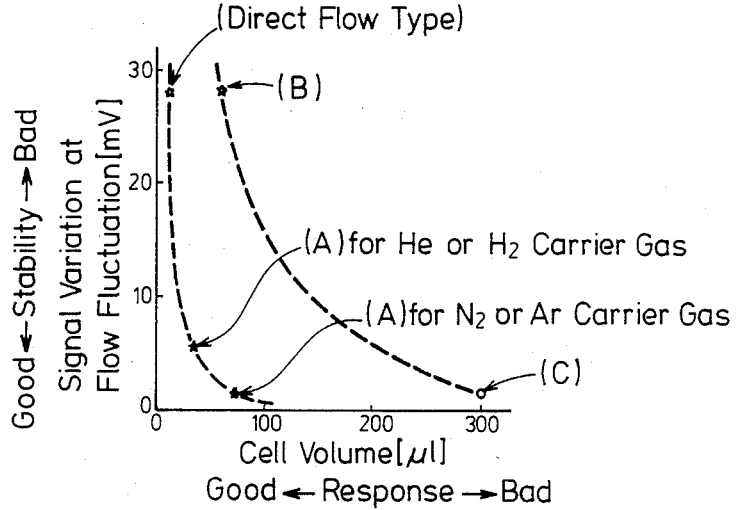
FIG. 7 is a graphic representation depicting the relation between magnitude of influence of flow fluctuation and cell volume for a conventional thermal conductivity detector and the invention.

FIG. 7 depicts a graph illustrating the examined results of the relations between magnitude of influence of flow fluctuations (stability) and cell volume (response), for each of the thermal conductivity detector tested. In preparing the graph, the carrier gas flux, in addition to the test requirements for preparing FIG. 6 6B,6C, was allowed to change between 2 ml/min and 40 ml/min.

As is evident from a comparison of FIG. 5C with FIGS. 5A and 5B, the height of the sharp peak (M$_2$,N$_2$, CO) in the conventional diffusion type detector was roughly half that in other detectors. The significance to this, is that the diffusion type detector is unable to provide sufficient detecting response. Moreover, as is evident from a comparison of FIG. 6B with FIGS. 6A and 6C, the conventional direct flow type detector produces noise about 5 to 10 times as much as that shown in FIGS. 6A or 6C, according to the switching of valves in connection with the above described CS and BF. Consequently, only the embodiment of this invention, is superior in both phases of detection and response (FIG. 5A) and noise properties (FIG. 6A). This is also proven in the graph shown in FIG. 7.

Figure 8A:
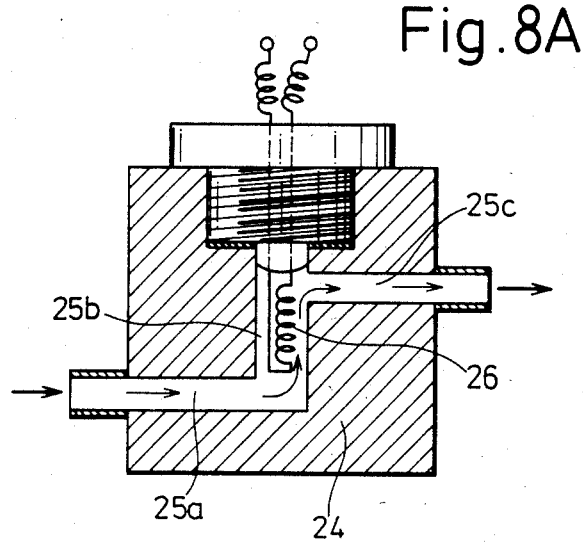
FIGS. 8A, 8B, 8C, 8D, and 8E are cross sectional views depicting principal portions of cells of alternative illustrative embodiments of the invention.
Figure 8B:
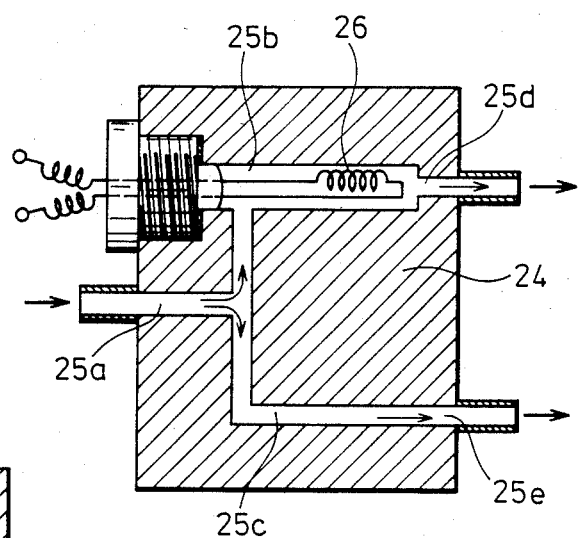
Figure 8C:
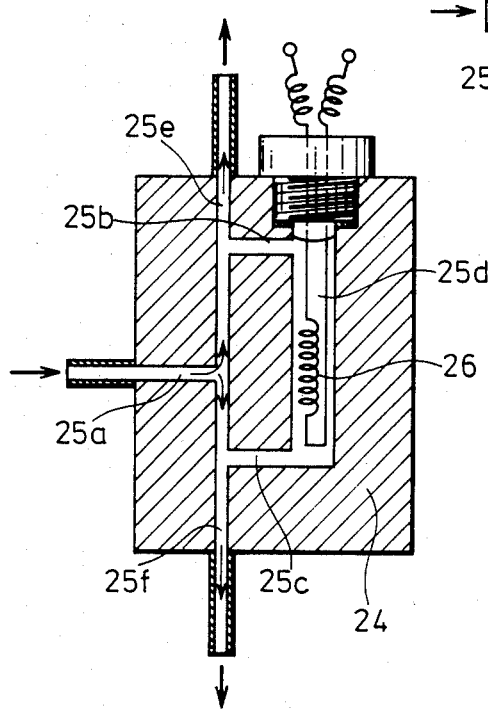
Figure 8D:
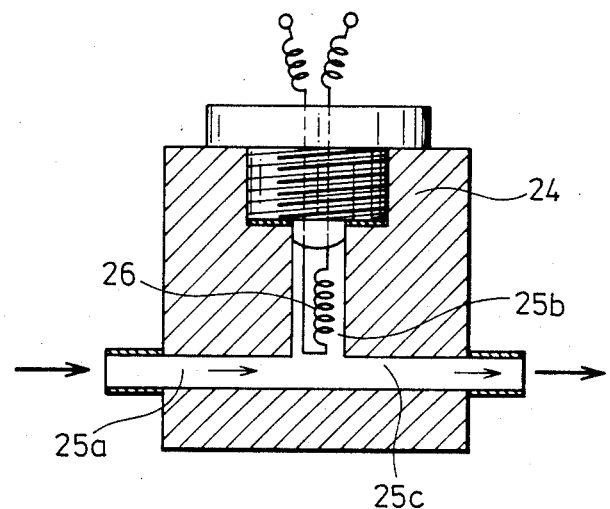
Figure 8E:
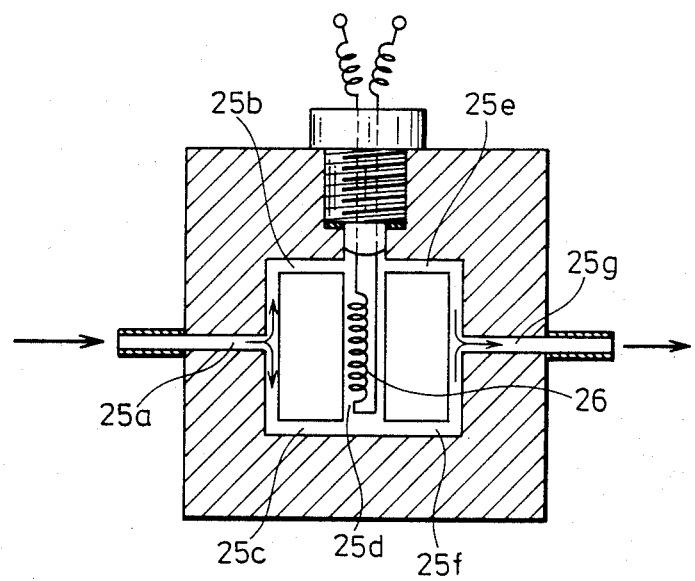

FIGS. 8A, 8B, 8C, 8D, and 8E, are cross sectional views of principal portions of other illustrative embodiments of the invention. FIGS. 8A and 8B depict direct flow type cells, and FIGS. 8C, 8D and 8E depict diffusion type cells.

In FIGS. 8A, 8B, 8C, 8D, and 8E, the predetermined fluid (which may be either the fluid being examined or the reference fluid) is made to directly or diffusively flow through internal flow passages 25a–25f, made in a desired shape, in block 24, in the direction shown by the arrow. In addition, a heater 26 formed of, for example, a filament, is arranged in a specified location, so that the thermal conductivity of the fluid can be detected.

Among the cells shown in FIGS. 8A, 8B, 8C, 8D, 8E, any two cells may be selected and used together. The same two cells as the ones selected are then prepared to make the total 4, that is these cells constitute the eleventh through fourteenth cells. In this case, the eleventh and twelveth cells have such cross sections as are shown in FIG. 8A, whereas the thirteenth and fourteenth cells have such cross sections as are shown in FIG. 8E. Thus, each of the pairs of direct flow type and diffusion type cells is often selected. These eleventh through fourteenth cells are respectively mounted as the first through fourth cells in FIG. 1. By changing the connections of the pipes to the inlet, the above first and second conditions may be obtained. For example, to obtain the first condition, the first pipe carrying the fluid to be examined is connected to inlet 5a, and the second pipe carrying the reference fluid is connected to inlet 6a. To obtain the second condition, the first pipe is connected to inlet 6a, and the second pipe is connected to inlet 5a.

As above described, the first and second cells have different internal flow passages from each other, and are respectively arranged in first and second flow passages, wherein the fluid being examined flows through the first passage and the reference fluid flows through the second passage. The advantage that accrues is thus that a thermal conductivity detector indicating detecting characteristics much more suitable for various uses than the conventional ones with cells having the same type of internal flow passages can now be materialized. In addition, advantageously, since the arranged positions of the first and second cells can be readily exchanged by the switching of the connections of the pipes. Also, advantageously, the inventive thermal conductivity detector can display a variety of detecting characteristics.

The foregoing description is illustrative of the principles of the invention. Numerous extensions and modifications thereof may be done by a person skilled in the art. All such extensions and modifications are to be construed to be within the spirit and scope of this invention.

What is claimed is:

1. A thermal conductivity detector comprising
   a pair of block structures, each block structure comprising
      a first through hole having two ends,
      a second through hole having two ends,
      a first bypass passageway having two ends,
      a second bypass passageway having two ends,
      an inlet means connecting one end of said first through hole, one end of said second through hole, one end of said first bypass passageway and one end of said second bypass passageway,
      an outlet means connecting another end of said first through hole, another end of said second through hole, another end of said first bypass passageway and another end of said second bypass passageway, and
      associated with each bock structure, a first heater disposed within said first through hole, and a second heater disposed within said second through hole;
   said detector further comprising means for connecting said first heater and said second heater of each block structure in an electrical bridge to detect thermal conductivity of a fluid to be measured using an unbalanced voltage of said bridge;
   wherein a fluid to be measured is applied to said inlet means in one block structure of said pair of block structures;
   wherein a reference fluid is applied to said inlet means in the other block structure of said pair of block structures;
   and wherein said first and second bypass passageways in said one block structure is different in internal diameter from said first and second bypass passageways in said other block structure.

2. The detector of claim 1, wherein said first through hole and said second through hole of each block structure is parallel to each other; and wherein said inlet means of each block structure comprises an inlet hole parallel to said first and second through holes, and a pair of inlet passageways connecting said inlet hole to said one end of said first and second through holes and to said one end of said first and second bypass passageways, said inlet passageways being disposed at 45° to said first and second through holes; and wherein said outlet means comprises an outlet hole parallel to said first and second through holes, and a pair of outlet passageways connecting said outlet hole to said other end of said first and second through holes and to said other end of said first and second bypass passageways, said outlet passageways being disposed at 45° to said first and second through holes; and wherein said first bypass passageway comprises a pair of flow passageways connected to each other and connected to said two ends of said first through hole at 45° with respect to said first through hole; and wherein said second bypass passageway comprises a pair of flow passageways connected to each other and connected to said two ends of said second through holes at 45° with respect to said second through hole.

* * * * *